(12) United States Patent
Sendai

(10) Patent No.: US 7,599,065 B2
(45) Date of Patent: Oct. 6, 2009

(54) SPECIMEN ANALYSIS SYSTEM OBTAINING CHARACTERISTIC OF SPECIMEN BY DIFFUSION APPROXIMATION

(75) Inventor: Tomonari Sendai, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 260 days.

(21) Appl. No.: 11/523,555

(22) Filed: Sep. 20, 2006

(65) Prior Publication Data

US 2007/0073158 A1   Mar. 29, 2007

(30) Foreign Application Priority Data

Sep. 20, 2005   (JP) .............................. 2005-272171

(51) Int. Cl.
*G01N 21/00* (2006.01)
*A61B 5/00* (2006.01)

(52) U.S. Cl. ....................................... 356/432; 600/310
(58) Field of Classification Search ............. 356/39–41, 356/432–440; 600/310, 316, 322
See application file for complete search history.

(56) References Cited

U.S. PATENT DOCUMENTS

| | | | | |
|---|---|---|---|---|
| 5,057,695 A | * | 10/1991 | Hirao et al. .................. 250/575 |
| 5,277,181 A | * | 1/1994 | Mendelson et al. ......... 600/322 |
| 5,372,135 A | * | 12/1994 | Mendelson et al. ......... 600/322 |
| 5,517,987 A | * | 5/1996 | Tsuchiya ..................... 600/328 |
| 5,770,454 A | * | 6/1998 | Essenpreis et al. .......... 436/164 |
| 5,772,588 A | * | 6/1998 | Miwa et al. .................. 600/310 |
| 5,825,488 A | * | 10/1998 | Kohl et al. ................... 356/342 |
| 6,615,061 B1 | * | 9/2003 | Khalil et al. ................. 600/310 |
| 6,704,110 B2 | * | 3/2004 | Tsuchiya ..................... 356/432 |

OTHER PUBLICATIONS

M. Vauhkonen, et al.. "Utilizing the Radiative Transfer Equation in Optical Tomography", OSA Biomedical Optics, pp. WF418-50, 2004.

* cited by examiner

*Primary Examiner*—Hoa Q Pham
(74) *Attorney, Agent, or Firm*—Sughrue Mion, PLLC

(57) ABSTRACT

In a specimen analysis system: incident light is injected into a specimen at an injection position on the specimen; an information acquisition unit acquires first information carried by light exiting from each of positions in a first region of the specimen in response to injection of the incident light into the specimen for a first duration of measurement, and second information carried by light exiting from each of positions in a second region of the specimen in response to injection of the incident light into the specimen for a second duration of measurement longer than the first duration of measurement; and an information processing unit calculates a characteristic of the specimen on the basis of the first and second information. The first region is located within a predetermined distance from the injection position, and the second region is located farther from the injection position than the first region.

20 Claims, 2 Drawing Sheets

“Utilizing the radiative transfer equation in optical tomography”, OSA Biomedical Optics, pp. WF48-50, 2004.

SPECIMEN ANALYSIS SYSTEM OBTAINING CHARACTERISTIC OF SPECIMEN BY DIFFUSION APPROXIMATION

BACKGROUND OF THE INVENTION

1. Field of the Invention

The present invention relates to a specimen analysis system which analyzes a characteristic of a specimen by injecting light into the specimen and acquiring information carried by light which propagates in and exits from the specimen.

2. Description of the Related Art

In recent years, the development of light absorption analysis (spectrometry) of a light-scattering substance such as a biological substance has been proceeding. The light applied to a light-scattering substance such as a biological substance undergoes multiple scattering and absorption in the light-scattering substance, and exits from the light-scattering substance. The behavior of light in a light-scattering substance can be expressed by an optical diffusion equation based on the optical diffusion theory, and the optical diffusion equation can be expressed as a differential equation. Therefore, it is possible to obtain a distribution of values of an optical characteristic such as an absorption coefficient, a scattering coefficient, or the like of a biological substance by measuring light which exits from the biological substance, and substituting the measured values in the optical diffusion equation.

For example, systems using the time-resolved spectroscopy and systems using the frequency-domain spectroscopy have been proposed as systems in which a distribution of optical characteristic values is obtained as above. The time-resolved spectroscopy uses ultra-short pulsed light having a width of approximately a picosecond, and the frequency-domain spectroscopy uses high-frequency modulated light.

According to the time-resolved spectroscopy, it is possible to obtain a distribution of optical characteristic values in a specimen of a light-scattering substance on the basis of the optical diffusion equation by injecting pulsed light into the specimen, and measuring the time spread (time profile) of the pulsed light which exits from the specimen after propagation through the specimen, where the time spread is caused by scattering of the pulsed light in the specimen.

According to the frequency-domain spectroscopy, it is possible to obtain a distribution of optical characteristic values in a specimen of a light-scattering substance on the basis of the optical diffusion equation by injecting high-frequency modulated light into the specimen, and measuring the intensity variation and phase delay at the modulation frequency in the light which exits from the specimen after propagation through the specimen, as disclosed by M. Vauhkonen et al., "Utilizing the radiative transfer equation in optical tomography", OSA Biomedical Optics, pp. WF48-50, 2004.

However, in the measurement of the light which exits from a specimen after propagation in the specimen for extracting information (such as a time profile or a combination of intensity variation and phase delay at the modulation frequency) carried by the light, when the optical propagation path of the light is long (i.e., when the distance from the injection position to the measurement position of the light is great), the intensity of the detected light is low, so that it is impossible to ensure sufficiently high signal-to-noise ratio. Therefore, the reliability of analysis performed by the conventional systems using the time-resolved spectroscopy or the frequency-domain spectroscopy is low.

SUMMARY OF THE INVENTION

The present invention has been developed in view of the above circumstances.

The object of the present invention is to provide a reliable specimen analysis system which can ensure sufficiently high signal-to-noise ratio and perform reliable analysis even when the distance from the injection position to the measurement position of light is great.

In order to accomplish the above object, a specimen analysis system according to the first aspect of the present invention is provided. The specimen analysis system according to the first aspect of the present invention comprises: a light injection unit which injects incident light into a specimen at an injection position on the specimen; an information acquisition unit which acquires first information carried by first light exiting from each of one or more positions in a first region of the specimen in response to injection of the incident light into the specimen for a first duration of measurement, and second information carried by second light exiting from each of one or more positions in a second region of the specimen in response to injection of the incident light into the specimen for a second duration of measurement longer than the first duration of measurement, where the first region is located within a predetermined distance from the injection position, and the second region is located farther from the injection position than the first region; and an information processing unit which calculates a characteristic of the specimen on the basis of the first and second information.

In the specimen analysis system according to the first aspect of the present invention, the first information carried by the first light which exits from each measurement position in the first region (within the predetermined distance of the injection position) is acquired during injection of the incident light for the first duration of measurement, and the second information carried by the second light which exits from each measurement position in the second region (farther from the injection position than the first region) is acquired during injection of the incident light for the second duration of measurement, and the second duration of measurements is longer than the first duration of measurement. Therefore, it is possible to ensure sufficiently high signal-to-noise ratio and improve the reliability of analysis even when the measurement position is remote from the injection position.

Preferably, the above specimen analysis system according to the first aspect of the present invention may further have the following additional features (i) to (v), (i) the first and second regions may be set in advance, for example, by inputting the predetermined distance into the specimen analysis system through some input means. Alternatively, the specimen analysis system may further comprise a region setting unit which sets the first and second regions before or during the measurement. For example, the region setting unit calculates a signal-to-noise ratio of information carried by light exiting from at least one position in the specimen, and sets the first and second regions according to the signal-to-noise ratio. In this case, it is possible to appropriately set the first and second regions according to the optical characteristic and the like of the specimen.

(ii) The second duration of measurement for which the incident light is injected into the specimen when the second light exiting from each of the one or more positions in the second region is acquired by the information acquisition unit increases stepwise with the distance between the injection position and the position in the second region. In this case, it is possible to more finely set the second duration of measurement to an appropriate length.

(iii) The specimen analysis system according to the first aspect of the present invention may further comprise an optical-intensity detection unit which detects the optical intensity of light exiting from at least one position in the first region, and sets the first duration of measurement on the basis of the detected optical intensity. In this case, it is possible to suppress unnecessary increase in the total measurement time.

(iv) The information acquisition unit successively acquires the first information carried by the first light exiting from each of the one or more positions in the first region and the second information carried by the second light exiting from each of the one or more positions in the second region. For example, the first and second information may be acquired by mechanically scanning the specimen with a single optical fiber, or by placing an array of optical fibers over the specimen and connecting an optical detection system or the like to the respective optical fibers in succession.

(v) The first light and the second light include fluorescence emitted from the specimen.

In addition, in order to accomplish the aforementioned object, a specimen analysis system according to the second aspect of the present invention is also provided. The specimen analysis system according to the second aspect of the present invention comprises: a light injection unit which injects pulsed light into a specimen at an injection position on the specimen; an information acquisition unit which acquires first information carried by first light exiting from each of one or more positions in a first region of the specimen in response to injection of a first number of pulses of the pulsed light into the specimen, and second information carried by second light exiting from each of one or more positions in a second region of the specimen in response to injection of a second number of pulses of the pulsed light into the specimen, where the first number is smaller than the second number, the first region is located within a predetermined distance from the injection position, and the second region is located farther from the injection position than the first region; and an information processing unit which calculates a characteristic of the specimen on the basis of the first information and the second information.

In the specimen analysis system according to the second aspect of the present invention, the first information carried by the first light which exits from each measurement position in the first region (within the predetermined distance of the injection position) is acquired during injection of the first number of pulses of the pulsed light, and the second information carried by the second light which exits from each measurement position in the second region (farther from the injection position than the first region) is acquired during injection of the second number of pulses of the pulsed light, and the second number is greater than the first number. Therefore, it is also possible to ensure sufficiently high signal-to-noise ratio and improve the reliability of analysis even when the measurement position is far from the injection position.

Preferably, the above specimen analysis system according to the second aspect of the present invention may further have the aforementioned additional features (i), (iv), and (v) and the following additional features (vi) and (vii).

(vi) The specimen analysis system according to the second aspect of the present invention, wherein the second number of the pulses of the pulsed light injected into the specimen when the second light exiting from each of the one or more positions in the second region is acquired by the information acquisition unit increases stepwise with the distance between the injection position and the position in the second region. In this case, it is possible to more finely set the second number to an appropriate value.

(vii) The specimen analysis system according to the second aspect of the present invention may further comprise an optical-intensity detection unit which detects the optical intensity of light exiting from at least one position in the first region, and sets the first number on the basis of the detected optical intensity. In this case, it is possible to suppress unnecessary increase in the total measurement time.

DESCRIPTION OF PREFERRED EMBODIMENTS

Figure 1:
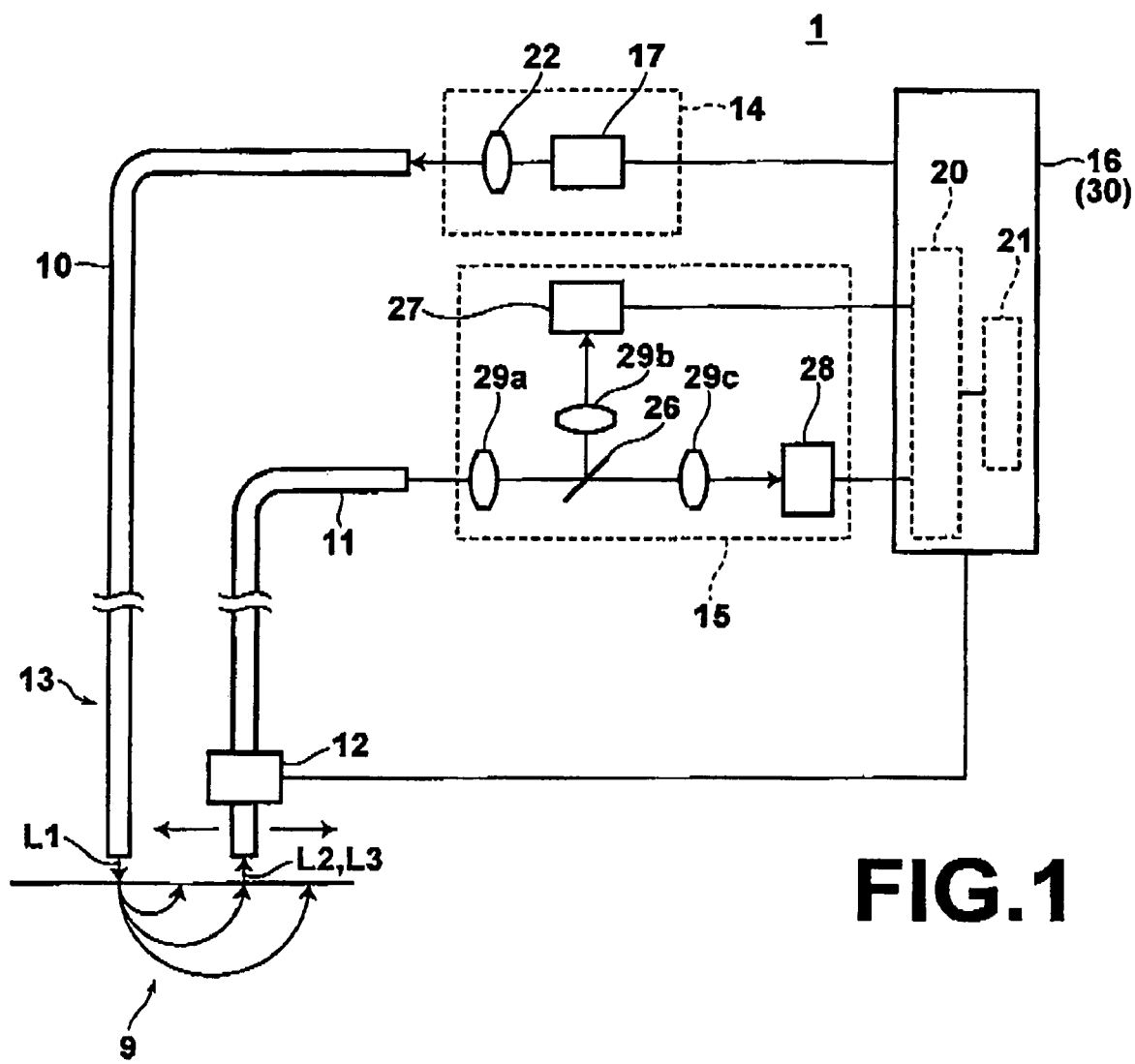
FIG. 1 is a diagram schematically illustrating a specimen analysis system according to a first embodiment of the present invention.

Preferred embodiments of the present invention are explained in detail below with reference to drawings. In the drawings, equivalent elements and constituents are indicated by the same reference numbers even in drawings for different embodiments, and descriptions of the equivalent elements or constituents are not repeated in the following explanations unless necessary.

First Embodiment

A specimen analysis system according to the first embodiment of the present invention is explained below with reference to FIG. 1, which schematically shows the construction of the specimen analysis system according to the first embodiment.

The specimen analysis system 1 according to the first embodiment injects pulsed incident light L1 through an injection optical fiber into an examined portion 9 of a subject, acquires information carried by light which exits from the examined portion 9 by scanning the examined portion 9 with a single measurement optical fiber, and measures a distribution of a fluorescent agent in the examined portion 9 by using the time-resolved spectroscopy, where the subject is dosed in advance with the fluorescent agent, the fluorescent agent has an affinity for a tumor, and the incident light L1 has a wavelength in the range which enables excitation of the fluorescent agent. In this example, the fluorescent agent emits fluorescence having the wavelengths of 770 to 790 nm when the fluorescent agent is excited by light having the wavelength of 750 nm.

As illustrated in FIG. 1, the specimen analysis system 1 according to the first embodiment comprises an optical probe unit 13, a light-source unit 14, a measurement unit 15, and a signal-processing-and-control unit 16.

The optical probe unit 13 is constituted by a light-injection optical fiber 10, a measurement optical fiber 11, and a scanning mechanism 12. The light-injection optical fiber 10 propagates the incident light L1, and the measurement optical fiber 11 propagates scattered light L2 and fluorescence L3 which exit from the examined portion 9. The scanning mechanism 12 realizes linear scanning of the examined portion 9 with the measurement optical fiber 11.

The light-injection optical fiber 10 is connected to the light-source unit 14, the measurement optical fiber 11 is connected to the measurement unit 15, and the light-source unit 14 and the measurement unit 15 are connected to the signal-processing-and-control unit 16.

Each of the light-injection optical fiber 10 and the measurement optical fiber 11 has a total diameter of 100 micrometers, a core diameter of 80 micrometers, and a cladding thickness of 10 micrometers.

The light-source unit 14 is constituted by a light source 17 and a lens 22. The light source 17 emits as the incident light L1 pulsed light having the wavelength of 750 nm, the pulse width of 100 ps, and the average power of 3 mW at the repetition rate of 100 MHz.

The measurement unit 15 comprises a dichroic mirror 26, photon-counting circuits 27 and 28, and lenses 29a, 29b, and 29c. The light which exits from the measurement optical fiber 11 is incident on the dichroic mirror 26 through the lens 29a in the measurement unit 15. When the wavelength of the light incident on the dichroic mirror 26 is equal to or longer than 760 nm, the light incident on the dichroic mirror 26 passes through the dichroic mirror 26. When the wavelength of the light incident on the dichroic mirror 26 is shorter than 760 nm, the dichroic mirror 26 reflects the light incident on the dichroic mirror 26 toward a direction perpendicular to the incident direction. The photon-counting circuit 27 counts the number of photons having a wavelength shorter than 760 nm and being detected during each measurement period, and the photon-counting circuit 28 counts the number of photons having a wavelength equal to or longer than 760 nm and being detected during each measurement period. Each of the photon-counting circuits 27 and 28 is constituted by a high-speed photodetector and a time-amplitude detector (TAC) (which are not shown), and measures the time difference between the timings of the injection of each light pulse and detection of a photon. The outputs of the photon-counting circuits 27 and 28 are supplied to the signal-processing unit 20 in the signal-processing-and-control unit 16.

The signal-processing-and-control unit 16 controls the overall operations of the specimen analysis system 1. Specifically, the signal-processing-and-control unit 16 comprises a signal-processing unit 20 and a distribution-calculation unit 21. The signal-processing unit 20 controls the specimen analysis system 1 so as to repeat injection of the incident light L1 and the measurement by the photon-counting circuits 27 and 28 a million times or two million times, produces time profiles on the basis of the measurement, and outputs the produced time profiles as information carried by the light. The distribution-calculation unit 21 calculates a distribution of the fluorescent agent in the examined portion 9 on the basis of the information outputted from the signal-processing unit 20. In addition, the signal-processing-and-control unit 16 controls the scanning mechanism 12 so as to linearly move the measurement optical fiber 11 by 100 micrometers every time a million pulses of the incident light L1 are injected, and repeats the injection of a million pulses of the incident light L1 and the movement of the measurement optical fiber 11 by 100 micrometers fifty times. Thereafter, the signal-processing-and-control unit 16 further controls the scanning mechanism 12 so as to move the measurement optical fiber 11 by 100 micrometers every time two million pulses of the incident light L1 are injected, and repeats the injection of two million pulses of the incident light L1 and the movement of the measurement optical fiber 11 by 100 micrometers fifty times. The other operations of the signal-processing-and-control unit 16 are explained later.

The operations of the specimen analysis system 1 according to the first embodiment are explained below.

First, the optical probe unit 13 is brought into contact with the examined portion 9 of the subject, who may have a tumor. Since the optical probe unit 13 is in contact with the examined portion 9 during measurement, the end of the optical probe unit 13 on the examined-portion side is protected by a transparent protective member (not shown). In the signal-processing-and-control unit 16, in advance, a region within 5 millimeters of the injection point of the incident light L1 is defined as the first region, and a region at distances of 5 to 10 millimeters from the injection point of the incident light L1 is defined as the second region.

Next, a measurement sequence is started under control of the signal-processing-and-control unit 16. In the measurement sequence explained below, measurement is first performed in the first region, and thereafter in the second region. The light source 17 in the light-source unit 14 emits the pulsed, incident light L1 having the wavelength of 750 nm, the pulse width of 100 picoseconds (ps), and the average power of 3 milliwatts (mW) at the repetition rate of 100 MHz. The signal-processing-and-control unit 16 controls the scanning mechanism 12 so that the measurement optical fiber 11 is initially located alongside the injection point of the incident light L1 and is then linearly moved away from the position alongside the injection position by 100 micrometers every time a million successive light pulses of the incident light L1 are injected through the light-injection optical fiber 10 into the examined portion 9. The injection of a million pulses of the incident light L1 and the movement of the measurement optical fiber 11 by 100 micrometers are repeated fifty times in succession.

Every time one of the million pulses of the incident light L1 is injected into the examined portion 9, scattered light L2 generated by scattering of the incident light L1 in the examined portion 9 and fluorescence L3 emitted from the fluorescent agent in the examined portion 9 propagate in and exit from the examined portion 9, and measurement of the scattered light L2 and the fluorescence L3 is performed by the measurement unit 15. Specifically, the scattered light L2 and the fluorescence L3 propagate through the measurement optical fiber 11 and enter the optical measurement unit 15. In the optical measurement unit 15, the scattered light L2 is reflected by the dichroic mirror 26 and enters the photon-counting circuit 27. On the other hand, the fluorescence L3 passes through the dichroic mirror 26 and enters the photon-counting circuit 28. The outputs of the photon-counting circuits 27 and 28 are supplied to the signal-processing unit 20 in the signal-processing-and-control unit 16.

Figure 2:
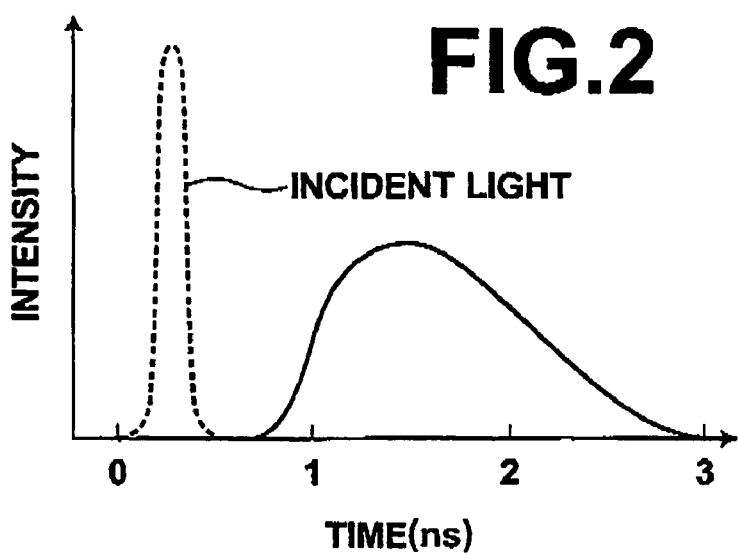
FIG. 2 is a graph indicating an example of a time profile obtained by the specimen analysis system according to the first embodiment.

While the measurement optical fiber 11 is located at each measurement position within 5 millimeters of the injection position of the light-injection optical fiber 10 (i.e., while the measurement optical fiber 11 is located at each measurement position in the first region), the signal-processing unit 20 produces a time profile (i.e., a time spread of light caused by scattering) as illustrated in FIG. 2 on the basis of the output of each of the photon-counting circuits 27 and 28 corresponding to the million pulses of the incident light L1, and the produced time profile is supplied to the distribution-calculation unit 21 as information carried by light which exits from the measurement position in the first region. The above operations for measurement are repeated at fifty measurement positions in the first region.

Thereafter, the signal-processing-and-control unit 16 controls the scanning mechanism 12 so that the measurement optical fiber 11 is moved by 100 micrometers every time two million pulses of the incident light L1 are injected into the examined portion 9, and the injection of two million pulses of the incident light L1 and the movement of the measurement optical fiber 11 by 100 micrometers are repeated fifty times. Every time one of the two million pulses of the incident light L1 is injected into the examined portion 9, measurement of the scattered light L2 and the fluorescence L3 is performed by the measurement unit 15, and the outputs of the photon-counting circuits 27 and 28 are supplied to the signal-processing unit 20 in the signal-processing-and-control unit 16. The signal-processing unit 20 also produces a time profile (i.e., a time spread of light caused by scattering) on the basis of the output of each of the photon-counting circuits 27 and 28 as illustrated in FIG. 2 for the two million pulses of the incident light L1, and the produced time profile is supplied to the distribution-calculation unit 21 as information carried by light which exits from each measurement position in the second region.

Thus, the distribution-calculation unit 21 produces, at each measurement position, a time profile of the incident light L1 which has propagated in the examined portion 9, on the basis of the measurement by the photon-counting circuit 27, and a time profile of the fluorescence (emitted from the fluorescent agent) which has propagated in the examined portion 9, on the basis of the measurement by the photon-counting circuit 28. Since the number of the measurement positions is one hundred, a hundred time profiles of the incident light L1 which has propagated in the examined portion 9 and a hundred time profiles of the fluorescence L3 which has propagated in the examined portion 9 are finally obtained.

After the above measurement, the distribution-calculation unit 21 performs signal processing of the hundred time profiles of the scattered light L2 on the basis of the optical diffusion equation, and calculates a distribution of the optical scattering coefficient and a distribution of the optical absorption coefficient in the examined portion 9 for the incident light L1 having the wavelength of 750 nm. Next, the distribution-calculation unit 21 calculates a distribution of the optical scattering coefficient and a distribution of the optical absorption coefficients for the fluorescence L3 having a wavelength of 770 to 790 nm on the basis of the distribution of the optical scattering coefficient and the distribution of the optical absorption coefficient for the incident light L1 having the wavelength of 750 nm. Thereafter, the distribution-calculation unit 21 calculates the distribution of the emission sources of the fluorescence L3 (i.e., the distribution of the fluorescent agent) on the basis of the distribution of the optical scattering coefficient and the distributions of the optical absorption coefficient for the fluorescence L3 having the wavelength of 770 to 790 nm, the hundred time profiles of the fluorescence L3 which has propagated in the examined portion 9, and the optical diffusion equation. The calculated distribution of the emission sources of the fluorescence L3 is outputted to a monitor (not shown) in the form of a tomographic image. Since the fluorescent agent has an affinity for a tumor, the tomographic image shows the shape of the tumor.

As mentioned before, in the specimen analysis system 1 according to the first embodiment, the distributions of optical characteristics in the examined portion 9 are calculated by using the time profiles based on the measurement of light at the hundred measurement positions, where each of the time profiles is obtained on the basis of the measurement with the hundred pulses of the incident light L1 when the measurement position is in the first range (i.e., the measurement optical fiber 11 is located within 5 mm of the injection position of the light-injection optical fiber 10), and on the basis of the measurement with the two hundred pulses of the incident light L1 when the measurement position is in the second range (i.e., the measurement optical fiber 11 is located at a distance greater than 5 mm from the injection position of the light-injection optical fiber 10). Therefore, the signal-to-noise ratio can be increased even when the measurement position is far from the injection position, so that it is possible to perform reliable analysis by using the specimen analysis system according to the first embodiment. In addition, since it is possible to achieve relatively high signal-to-noise ratio in the first region, the number (one hundred) of the pulses of the incident light L1 used in the measurement of light at each measurement position in the first region is smaller than the number (two hundred) of the pulses of the incident light L1 used in the measurement of light at each measurement position in the second region. Therefore, the total measurement time can be suppressed.

The specimen analysis system 1 according to the first embodiment may be modified as follows.

Although the measurement optical fiber 11 is one-dimensionally moved in the above explanations of the specimen analysis system 1 according to the first embodiment, it is possible to two-dimensionally move the measurement optical fiber 11. In this case, it is possible to obtain three-dimensional tomographic images.

The signal-processing-and-control unit 16 in the specimen analysis system 1 according to the first embodiment may be replaced with a signal-processing-and-control unit 30, which operates as follows. Although the boundary between the first and second regions is set in advance in the signal-processing-and-control unit 16, the signal-processing-and-control-unit 30 calculates signal-to-noise ratios of the information which is carried by light and obtained from the light by measurement of the light at the measurement positions, and sets the boundary between the first and second regions according to the calculated signal-to-noise ratios. Specifically, the signal-processing-and-control unit 30 may operate in one of the following manners (a) to (d).

(a) After the measurement sequence is started, the signal-processing-and-control unit 30 calculates the average and the standard deviation of the intensities in the vicinities of the peaks of the time profiles at each measurement position in the entire measurement sequence, and obtains the ratio of the average and the standard deviation as the signal-to-noise ratio. When the ratio of the average and the standard deviation is equal to or lower than a predetermined value (e.g., ten), the signal-processing-and-control unit 30 determines that the signal-to-noise ratio is low, and increases the number of the pulses of the incident light L1 used in measurement at the subsequent measurement positions to two million in order to increase the signal-to-noise ratio.

(b) The signal-processing-and-control unit 30 compares first information which is carried by first light and obtained from the first light by the measurement at each measurement position and second information which is carried by second light and obtained from the second light by the measurement at an adjacent measurement position, and sets the boundary between the first and second regions according to the comparison result. Specifically, after the measurement sequence is started, the signal-processing-and-control unit 30 calculates a time profile on the basis of the measurement of the light at each measurement position, and compares the time profile calculated at the measurement position with a time profile which is precedingly obtained on the basis of measurement of light at an adjacent measurement position. When the compared time profiles are approximately identical, the signal-processing-and-control unit 30 increases the number of the pulses of the incident light L1 used in measurement at the subsequent measurement positions in order to increase the signal-to-noise ratio. Generally, as the measurement position moves farther apart from the injection position, the signal-to-noise ratio deteriorates, and the difference between the compared time profiles decreases. Therefore, when the compared time profiles become approximately identical, the signal-to-noise ratio is increased by increasing the number of the pulses of the incident light L1 used in measurement at the subsequent measurement positions. Since the boundary between the first and second regions is set according to the signal-to-noise ratio of the information carried by the measured light, it is possible to set the boundary between the first and second regions according to an optical characteristic or the like of the specimen.

(c) The signal-processing-and-control unit 30 calculates the optical intensity in at least one time profile obtained on the basis of the measurement of the light at at least one measurement position immediately after the start of the measurement sequence, and sets the number of the pulses of the incident light L1 used in the measurement at each measurement position according to the calculated optical intensity.

For example, when the optical intensity is low, it is possible to use two million pulses of the incident light L1 for production of time profiles at each measurement position even in the vicinity of the injection position, and thereafter further increases the number of the pulses of the incident light L1 to four million.

Alternatively, when the optical intensity is high, in order to suppress unnecessary increase in the total measurement time, the signal-processing-and-control unit 30 may initially use fifty thousand pulses of the incident light L1 for production of time profiles at each measurement position, and thereafter use a million pulses of the incident light L1 for production of time profiles at each of the subsequent measurement positions.

Further alternatively, the signal-processing-and-control unit 30 may calculate the optical intensity in a time profile obtained on the basis of the measurement of the light at each measurement position, and stepwise or continuously increase the number of the pulses of the incident light L1 used in the measurement at each measurement position according to the calculated optical intensity.

(d) The signal-processing-and-control unit 30 calculates the optical intensity of the measured light at each measurement position, and stepwise or continuously increases the the number of the pulses of the incident light L1 used in the measurement at each measurement position according to the optical intensity. Alternatively, the signal-processing-and-control unit 30 may stepwise or continuously increase the number of the pulses of the incident light L1 used in the measurement at each measurement position according to the signal-to-noise ratio, or the distance from the injection position to the measurement position.

Second Embodiment

A specimen analysis system according to the second embodiment of the present invention is explained below with reference to FIG. 3, which schematically shows the construction of the specimen analysis system according to the second embodiment.

The specimen analysis system 2 according to the second embodiment injects incident light L4 through an injection optical fiber into an examined portion 9 of a subject, acquires information carried by light which exits from the examined portion 9 by scanning the examined portion 9 with a single measurement optical fiber, and measures a distribution of a fluorescent agent in the examined portion 9 by using the frequency-domain spectroscopy, where the subject is dosed in advance with the fluorescent agent, the fluorescent agent has an affinity for a tumor, and the incident light L4 has a wavelength in the range which enables excitation of the fluorescent agent, and is modulated at a high frequency.

Figure 3:
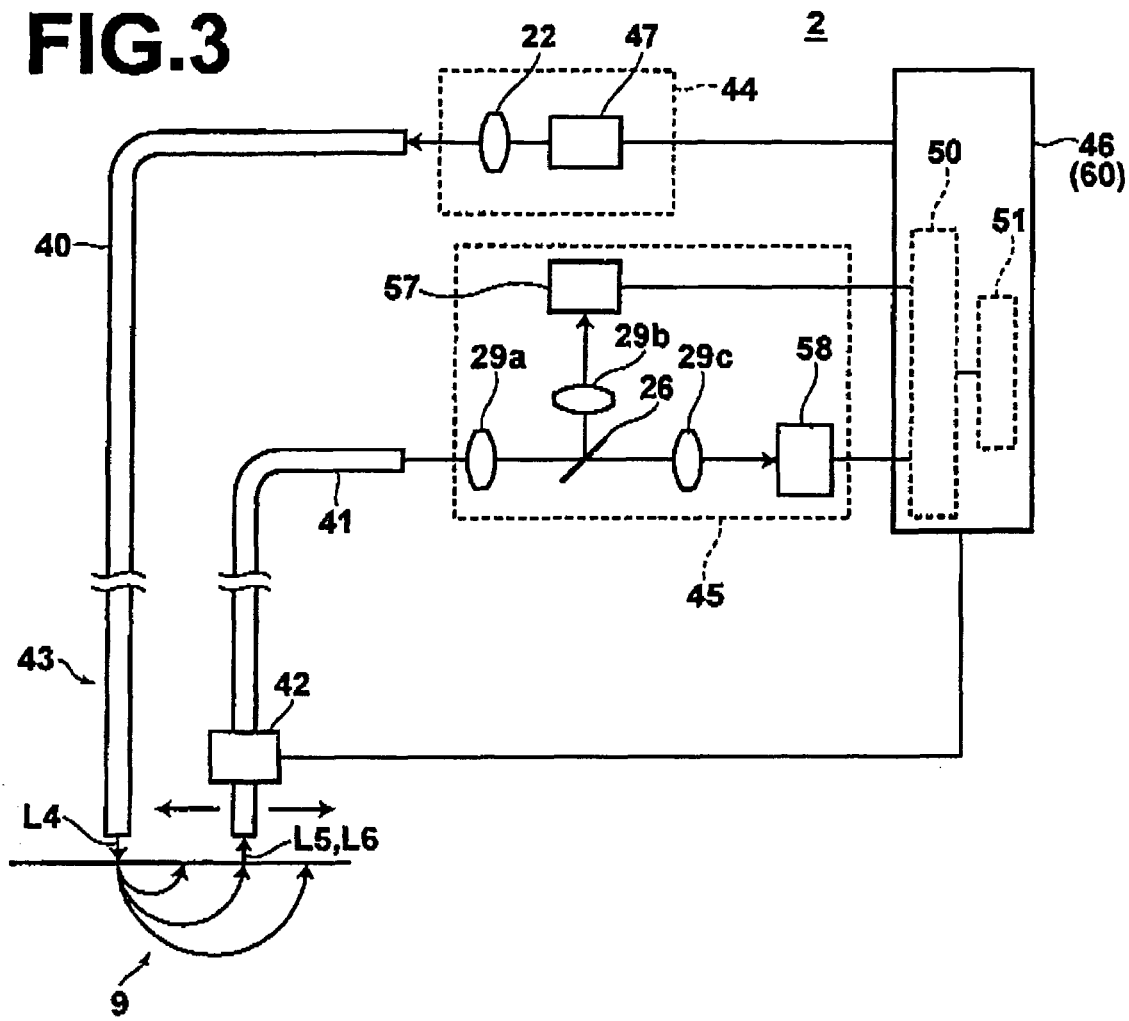
FIG. 3 is a diagram schematically illustrating a specimen analysis system according to a second embodiment of the present invention.

As illustrated in FIG. 3, the specimen analysis system 2 according to the second embodiment comprises an optical probe unit 43, a light-source unit 44, a measurement unit 45, and a signal-processing-and-control unit 46.

The optical probe unit 43 is constituted by a light-injection optical fiber 40, a measurement optical fiber 41, and a scanning mechanism 42. The light-injection optical fiber 40 propagates the incident light L4, and the measurement optical fiber 41 propagates scattered light L5 and fluorescence L6 which exit from the examined portion 9. The scanning mechanism 42 realizes linear scanning of the examined portion 9 with the measurement optical fiber 41.

The light-injection optical fiber 40 is connected to the light-source unit 44, the measurement optical fiber 41 is connected to the measurement unit 45, and the light source unit 44 and the measurement unit 45 are connected to the signal-processing-and-control unit 46.

Each of the light-injection optical fiber 40 and the measurement optical fiber 41 has a total diameter of 100 micrometers, a core diameter of 80 micrometers, and a cladding thickness of 10 micrometers.

The light-source unit 44 is constituted by a light source 47 and a lens 22. The light source 47 is realized by a semiconductor laser, and emits as the incident light L4 modulated light having the wavelength of 750 nm and the average power of 3 mW and being modulated at the frequency of 100 MHz.

The measurement unit 45 comprises a dichroic mirror 26, photodetectors 57 and 58, and lenses 29a, 29b, and 29c. The light which exits from the measurement optical fiber 41 is incident on the dichroic mirror 26 through the lens 29a in the measurement unit 45. When the wavelength of the light incident on the dichroic mirror 26 is equal to or longer than 760 nm, the light incident on the dichroic mirror 26 passes through the dichroic mirror 26. When the wavelength of the light incident on the dichroic mirror 26 is shorter than 760 nm, the dichroic mirror 26 reflects the light incident on the dichroic mirror 26 toward a direction perpendicular to the incident direction. The photodetector 57 detects light having a wavelength shorter than 760 nm during each measurement period, and the photodetector 58 detects light having a wavelength equal to or longer than 760 nm during each measurement period. The outputs of the photodetectors 57 and 58 are supplied to the signal-processing unit 50 in the signal-processing-and-control unit 46.

Figure 4:
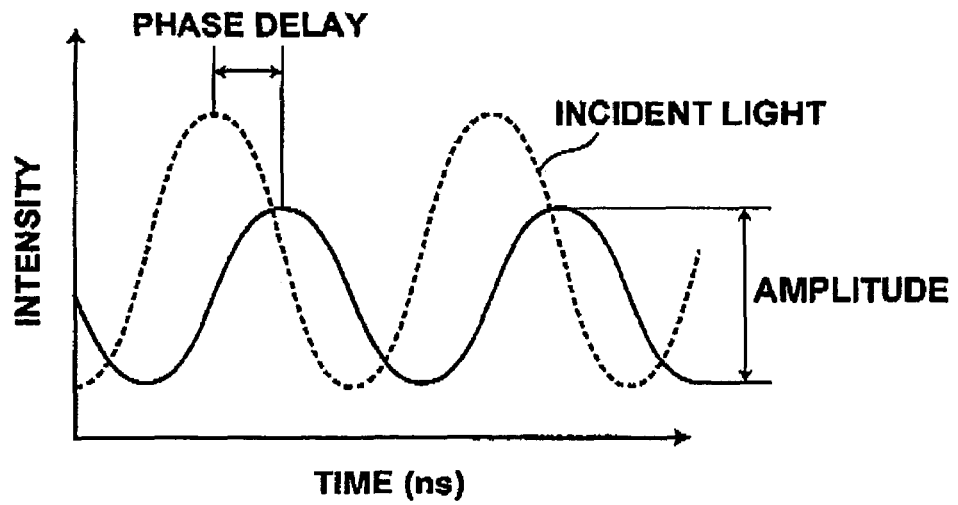
FIG. 4 is a graph indicating examples of the amplitude and the phase delays detected in the specimen analysis system according to the second embodiment.

The signal-processing-and-control unit 46 controls the overall operations of the specimen analysis system 2. Specifically, the signal-processing-and-control unit 46 comprises a signal-processing unit 50 and a distribution-calculation unit 51. The signal-processing unit 50 calculates information being carried by light and including an amplitude and a phase delay as illustrated in FIG. 4, on the basis of the outputs of the photodetectors 57 and 58 for a duration of 1 millisecond or 2 milliseconds at each measurement position. The signal-processing unit 51 calculates a distribution of the fluorescent agent in the examined portion 9 on the basis of the information calculated by the signal-processing unit 50. The signal-processing-and-control unit 46 controls the scanning mechanism 42 so as to initially locate the detection optical fiber 41 alongside the injection position of the incident light L4, linearly move the measurement optical fiber 41 by 100 micrometers every time the incident light L4 is injected into the examined portion 9 for 1 millisecond, and repeat the injection of the incident light L4 for 1 millisecond and the movement of the measurement optical fiber 41 by 100 micrometers fifty times. Thereafter, the signal-processing-and-control unit 46 further controls the scanning mechanism 42 so as to move the measurement optical fiber 41 by 100 micrometers every time the incident light L4 is injected into the examined portion 9 for 2 milliseconds, and repeat the injection of the incident light L4 for 2 milliseconds and the movement of the measurement optical fiber 41 by 100 micrometers fifty times. The other operations of the signal-processing-and-control unit 46 are explained later.

The operations of the specimen analysis system 2 according to the second embodiment are explained below.

First, the optical probe unit 43 is brought into contact with the examined portion 9 of the subject, who may have a tumor. Since the optical probe unit 43 is in contact with the examined portion 9 during measurement, the end of the optical probe unit 43 on the examined-portion side is protected by a transparent protective member (not shown). In the signal-processing-and-control unit 46, in advance, a region within 5 millimeters of the injection position of the incident light L4 is defined as the first region, and a region at distances of 5 to 10 millimeters from the injection position of the incident light L4 is defined as the second region.

Next, a measurement sequence is started under control of the signal-processing-and-control unit 46. In the measurement sequence explained below, measurement is first performed in the first region, and thereafter in the second region. The light source 47 in the light-source unit 44 emits the incident light L4 having the wave length of 750 nm and the average power of 3 mW and being modulated at the frequency of 100 MHz. The signal-processing-and-control unit 46 controls the scanning mechanism 42 so that the measurement optical fiber 41 is initially located alongside the injection position of the incident light L4, and is then linearly moved away from the position alongside the injection position by 100 micrometers every time the incident light L4 is injected into the examined portion 9 for 1 millisecond. The injection of the incident light L4 for 1 millisecond and the movement of the measurement optical fiber 41 by 100 micrometers are repeated fifty times in succession.

The operations of the measurement unit 45 for measurement are performed in synchronization with the timing of the movement of the detection optical fiber 41 as follows. When the incident light L4 is injected into the examined portion 9, scattered light L5 generated by scattering of the incident light L4 in the examined portion 9 and fluorescence L6 emitted from the fluorescent agent in the examined portion 9 propagate in and exit from the examined portion 9, and measurement of the scattered light L5 and the fluorescence L6 is performed by the measurement unit 45. The scattered light L5 and the fluorescence L6 propagate through the measurement optical fiber 41 and enter the optical measurement unit 45. In the optical measurement unit 45, the scattered light L5 is reflected by the dichroic mirror 26 and enters the photodetector 57. On the other hand, the fluorescence L6 passes through the dichroic mirror 26 and enters the photodetector 58. The outputs of the photodetectors 57 and 58 are supplied to the signal-processing unit 50 in the signal-processing-and-control unit 46.

While the measurement optical fiber 41 is located at each measurement position within 5 millimeters of the injection position of the light-injection optical fiber 40 (i.e., while the measurement optical fiber 41 is located at each measurement position in the first region), the signal-processing unit 50 calculates the amplitude and the phase delay in the scattered light L5 on the basis of the outputs of the photodetectors 57 and 58 for the duration of 1 millisecond, and outputs the calculated amplitude and phase delay to the signal-processing unit 51.

Thereafter, the signal-processing-and-control unit 46 controls the scanning mechanism 42 so that the measurement optical fiber 41 is further moved by 100 micrometers every time the incident light L4 is injected into the examined portion 9 for 2 milliseconds, and the injection of the incident light L4 for 2 milliseconds and the movement of the detection optical fiber 41 by 100 micrometers are repeated fifty times.

While the measurement optical fiber 41 is located at each measurement position at a distance greater than 5 millimeters and smaller than 10 millimeters from the injection position of the light-injection optical fiber 40 (i.e., while the measurement optical fiber 41 is located at each measurement position in the second region), the signal-processing unit 50 calculates the amplitude and the phase delay in the scattered light L5 on the basis of the outputs of the photodetectors 57 and 58 for the duration of 2 milliseconds, and outputs the calculated amplitude and phase delay to the signal-processing unit 51.

The signal-processing unit 51 calculates the optical scattering coefficient and the optical absorption coefficient in the examined portion 9 for the incident light L4 (having the wavelength of 750 nm) on the basis of the amplitudes and the phase delays of the scattered light L5 calculated at the respective measurement positions. Then, the distribution-calculation unit 51 calculates the optical scattering coefficient and the optical absorption coefficient in the examined portion 9 for the fluorescence L6 having a wavelength of 770 to 790 nm on the basis of the optical scattering coefficient and the optical absorption coefficient for the fluorescence L4. Thereafter, the distribution-calculation unit 51 calculates the distribution of the emission sources of the fluorescence L6 (i.e. the distribution of the fluorescent agent) on the basis of the optical scattering coefficient and the optical absorption coefficient for the fluorescence L6, the amplitudes and the phase delays of the fluorescence L6, and the optical diffusion equation. The calculated distribution of the emission sources of the fluorescence L6 is outputted to a monitor (not shown) in the form of a tomographic image. Since the fluorescent agent has an affinity for a tumor, the tomographic image shows the shape of the tumor.

As mentioned before, in the specimen analysis system 2 according to the second embodiment, the signal-processing unit 50 calculates a distribution of optical characteristic values in the examined portion 9 on the basis of the information obtained from light measured for 1 millisecond at each measurement position when the measurement optical fiber 41 is located within 5 millimeters of the injection position of the light-injection optical fiber 40 (i.e., when the measurement optical fiber 41 is located in the first region), and on the basis of the information obtained from light measured for 2 milliseconds at each measurement position when the measurement optical fiber 41 is located at a distance greater than 5 millimeters and smaller than 10 millimeters from the injection position of the light-injection optical fiber 40 (i.e., when the measurement optical fiber 41 is located in the second region). Therefore, it is possible to increase the signal-to-noise ratio even when the measurement position is relatively far from the injection position of the incident light L4, and thus perform highly reliable analysis. In addition, since the information obtained from light measured for 1 millisecond is used when the measurement position is in the first region (in which relatively high signal-to-noise ratio can be ensured), it is possible to suppress increase in the total measurement time.

The specimen analysis system 2 according to the second embodiment may be modified as follows.

Although the measurement optical fiber 41 is one-dimensionally moved in the above explanations of the specimen analysis system 2 according to the second embodiment, it is possible to two-dimensionally move the measurement optical fiber 41. In this case, it is possible to obtain three-dimensional tomographic images.

The signal-processing-and-control unit 46 in the specimen analysis system 2 according to the second embodiment may be replaced with a signal-processing-and-control-unit 60, which operates in one of the following manners (a) to (d).

(a) The signal processing-and-control unit 60 calculates the difference between first information (the amplitude and/or the phase delay) which is carried by first light and obtained from the first light by measurement at each measurement position and second information (the amplitude and/or the phase delay) which is carried by second light and obtained from the second light by measurement at an adjacent measurement position. When the difference between the first and second information is equal to or smaller than a predetermined amount, the signal-processing-and-control unit 60 increases the durations of measurement in the subsequent measurement positions, so that the first and second regions can be appropriately set according to an optical characteristic or the like of the specimen. For example, the above difference may be the difference between the phase delay D1 obtained at each measurement position and the phase delay D2 obtained at an adjacent measurement position. Alternatively, the signal-processing-and-control unit 60 may increase the durations of measurement in the subsequent measurement positions when the phase delays D1 and D2 satisfy the following inequalities.

$$-0.01 < (D1-D2) \div (D1+D2) \div 2 < 0.01$$

(b) After the measurement sequence is started, the signal-processing-and-control unit 60 calculates the average and the standard deviation of the phase delays at each measurement position, and obtains the ratio of the average and the standard deviation as the signal-to-noise ratio. When the ratio of the average and the standard deviation is equal to or lower than a predetermined value (e.g., 10 dB), the signal-processing-and-control unit 60 determines that the signal-to-noise ratio is low, and increases the durations of measurement at the subsequent measurement positions to increase the signal-to-noise ratio. Since the boundary between the first and second regions is set according to the signal-to-noise ratio of the information carried by the measured light, it is possible to set the boundary between the first and second regions according to the optical characteristic or the like of the specimen.

(c) The signal-processing-and-control unit 60 calculates the optical intensity in at least one time profile obtained on the basis of the measurement of the light at at least one measurement position immediately after the start of the measurement sequence, and sets the durations of measurement according to the calculated optical intensity.

For example, when the optical intensity is low, it is possible to in initially set the duration of measurement at each measurement position to 2 milliseconds, and thereafter increase the duration of measurement to 4 milliseconds. Alternatively, when the optical intensity is high, in order to suppress unnecessary increase in the total measurement time, it is possible to initially set the duration of measurement to 0.5 milliseconds at each measurement position, and thereafter increase the duration of measurement to 1 millisecond.

(d) The signal-processing-and-control unit 60 calculates the optical intensity of the measured light at each measurement position, and stepwise or continuously increases the duration of measurement at each measurement position according to the optical intensity. Alternatively, the signal-processing-and-control unit 60 may stepwise or continuously increase the duration of measurement at each measurement position according to the signal-to-noise ratio, or the distance from the injection position to the measurement position.

Additional Matters

Although the measurement is started from the vicinity of the injection position of the incident light in the first and second embodiments, alternatively, it is possible to start the measurement from a position remote from the injection position. In this case, it is possible to achieve the aforementioned advantages by successively decreasing the number of the pulses of the incident light L1 used in the measurement at each measurement position or the duration of measurement at each measurement position.

What is claimed is:

1. A specimen analysis system comprising:
    a light injection unit which injects incident light into a specimen at an injection position on the specimen,
        wherein the light injection unit injects incident light for a first injection duration to produce first light exiting from each of one or more positions in a first region of the specimen, and
        wherein the light injection unit injects incident light for a second injection duration to produce second light exiting from each of one or more positions in a second region of the specimen;
    an information acquisition unit which acquires first information carried by the first light exiting from each of the one or more positions in the first region of said specimen in response to injection of said incident light into the specimen for the first injection duration, and second information carried by the second light exiting from each of the one or more positions in the second region of the specimen in response to injection of said incident light into the specimen for the second injection duration,
        wherein the second injection duration is longer than the first injection duration, and
        wherein the first region is located within a predetermined distance from said injection position, and the second region is located farther from the injection position than the first region; and
    an information processing unit which calculates a characteristic of said specimen on the basis of said first information and said second information.

2. A specimen analysis system according to claim 1, further comprising a region setting unit which calculates a signal-to-noise ratio of information carried by light exiting from at least one position in said specimen, and sets said first region and said second region according to the signal-to-noise ratio.

3. A specimen analysis system according to claim 2, further comprising an optical-intensity detection unit which detects an optical intensity of light exiting from at least one position in said first region, and sets said first injection duration on the basis of the detected optical intensity.

4. A specimen analysis system according to claim 1, wherein said second injection duration for which the incident light is injected into the specimen when said second light exiting from each of said one or more positions in the second region is acquired by said information acquisition unit increases stepwise with a distance between said injection position and said each of the one or more positions in the second region.

5. A specimen analysis system according to claim 4, further comprising an optical-intensity detection unit which detects an optical intensity of light exiting from at least one position in said first region, and sets said first injection duration on the basis of the detected optical intensity.

6. A specimen analysis system according to claim 1, further comprising an optical-intensity detection unit which detects an optical intensity of light exiting from at least one position in said first region, and sets said first injection duration on the basis of the detected optical intensity.

7. A specimen analysis system according to claim 1, wherein said information acquisition unit successively acquires said first information carried by said first light exiting from each of said one or more positions in said first region and said second information carried by said second light exiting from each of said one or more positions in said second region.

8. A specimen analysis system according to claim 1, wherein said first light and said second light include fluorescence emitted from said specimen.

9. A specimen analysis system according to claim 1, further comprising a scanning mechanism, which moves the information acquisition unit from one or more positions in at least one of the first region and the second region to one or more positions in the second region and the first region, respectively.

10. A specimen analysis system comprising:
a light injection unit which injects pulsed light into a specimen at an injection position on the specimen;
an information acquisition unit which acquires first information carried by first light exiting from each of one or more positions in a first region of said specimen in response to injection of a first number of pulses of said pulsed light into the specimen, and second information carried by second light exiting from each of one or more positions in a second region of the specimen in response to injection of a second number of pulses of said pulsed light into the specimen, where the first number is smaller than the second number, the first region is located within a predetermined distance from said injection position, and the second region is located farther from the injection position than the first region; and
an information processing unit which calculates a characteristic of said specimen on the basis of said first information and said second information.

11. A specimen analysis system according to claim 10, further comprising a region setting unit which calculates a signal-to-noise ratio of information carried by light exiting from at least one position in said specimen, and sets said first region and said second region according to the signal-to-noise ratio.

12. A specimen analysis system according to claim 11, further comprising an optical-intensity detection unit which detects an optical intensity of light exiting from at least one position in said first region, and sets said first number on the basis of the detected optical intensity.

13. A specimen analysis system according to claim 10, wherein said second number of said pulses of the pulsed light injected into the specimen when said second light exiting from each of said one or more positions in the second region is acquired by said information acquisition unit increases stepwise with a distance between said injection position and said each of the one or more positions in the second region.

14. A specimen analysis system according to claim 13, further comprising an optical-intensity detection unit which detects an optical intensity of light exiting from at least one position in said first region, and sets said first number on the basis of the detected optical intensity.

15. A specimen analysis system according to claim 10, further comprising an optical-intensity detection unit which detects an optical intensity of light exiting from at least one position in said first region, and sets said first number on the basis of the detected optical intensity.

16. A specimen analysis system according to claim 10, wherein said information acquisition unit successively acquires said first information carried by said first light exiting from each of said one or more positions in said first region and said second information carried by said second light exiting from each of said one or more positions in said second region.

17. A specimen analysis system according to claim 10, wherein said first light and said second light include fluorescence emitted from said specimen.

18. A specimen analysis system according to claim 10, further comprising a scanning mechanism, which moves the information acquisition unit from one or more positions in at least one of the first region and the second region to one or more positions in the second region and the first region, respectively.

19. The specimen analysis system according to claim 10, wherein the light injection unit injects the first number of pulses of pulsed incident light into the specimen to produce the first light exiting from each of the one or more positions in the first region of the specimen, and
wherein the light injection unit injects the second number of pulses of pulsed incident light into the specimen to produce second light exiting from each of the one or more positions in the second region of the specimen.

20. A specimen analysis system comprising:
a light injection unit which injects incident light into a specimen at an injection position on the specimen;
an information acquisition unit which acquires first information carried by first light exiting from each of one or more positions in a first region of said specimen in response to injection of said incident light into the specimen for a first duration of measurement, and second information carried by second light exiting from each of one or more positions in a second region of the specimen in response to injection of said incident light into the specimen for a second duration of measurement longer than the first duration of measurement, where the first region is located within a predetermined distance from said injection position, and the second region is located farther from the injection position than the first region
wherein the information acquisition unit comprises:
a first photodetector positioned at each of the one or more positions in the first region of the specimen, which calculates amplitudes and phase delays of scattered light and outputs signals for the first duration of measurement, and
a second photodetector positioned at each of the one or more positions in the second region of the specimen, which calculates amplitudes and phase delays of scattered light and outputs signals for the second duration of measurement; and
an information processing unit which calculates a characteristic of said specimen on the basis of said first information and said second information.

* * * * *